(12) United States Patent
Ferguson

(10) Patent No.: US 7,745,681 B1
(45) Date of Patent: Jun. 29, 2010

(54) NONWOVEN FABRICS AND THEIR MANUFACTURE AND USE

(75) Inventor: Paul John Ferguson, Walsgrave (GB)

(73) Assignee: ConvaTec Limited, Deeside, Flintshire (GB)

( * ) Notice: Subject to any disclaimer, the term of this patent is extended or adjusted under 35 U.S.C. 154(b) by 0 days.

(21) Appl. No.: 09/701,103

(22) PCT Filed: Jun. 21, 1999

(86) PCT No.: PCT/GB99/01945

§ 371 (c)(1),
(2), (4) Date: Nov. 22, 2000

(87) PCT Pub. No.: WO99/67456

PCT Pub. Date: Dec. 29, 1999

(30) Foreign Application Priority Data

Jun. 23, 1998 (GB) ................................. 9813529.6

(51) Int. Cl.
*A61F 13/00* (2006.01)
*A61F 13/15* (2006.01)
*B32B 27/32* (2006.01)
*B32B 5/26* (2006.01)
*D04H 1/46* (2006.01)

(52) U.S. Cl. .............................. 602/43; 602/42; 602/45; 428/219; 428/220; 442/50; 442/402; 442/381; 442/383; 442/385

(58) Field of Classification Search ................ 442/402, 442/50, 381, 383, 385; 602/45, 42, 43; 604/304, 604/367

See application file for complete search history.

(56) References Cited

U.S. PATENT DOCUMENTS

| 4,977,892 | A | * | 12/1990 | Ewall .......................... 604/364 |
| 5,115,801 | A |   | 5/1992  | Cartmell ....................... 602/48 |
| 5,197,945 | A | * | 3/1993  | Cole et al. .................... 602/49 |
| 5,238,685 | A | * | 8/1993  | Wren .......................... 424/445 |
| 5,643,653 | A | * | 7/1997  | Griesbach et al. ........... 428/120 |
| 5,674,524 | A |   | 10/1997 | Scherr ........................ 424/445 |
| 5,714,232 | A |   | 2/1998  | Fenton ........................ 428/171 |
| 5,731,083 | A |   | 3/1998  | Bahia ......................... 428/393 |

FOREIGN PATENT DOCUMENTS

| CA | 2097264 A | 12/1993 |
| CA | 2100133 A | 1/1994 |
| EP | 344913 A | 12/1989 |
| EP | 476756 A | 3/1992 |
| EP | 572891 A | 12/1993 |
| EP | 578107 A | 1/1994 |
| GB | 1379158 A | 1/1975 |
| GB | 1394742 A | 5/1975 |
| GB | 2221620 A | 2/1990 |
| WO | WO89/12471 A | 12/1989 |
| WO | WO93/12275 A | 6/1993 |

OTHER PUBLICATIONS

Dictionary of Textiles, p. 499, "Screw", 7th Ed.*

* cited by examiner

*Primary Examiner*—Lynda Salvatore
(74) *Attorney, Agent, or Firm*—John M. Kilcoyne

(57) ABSTRACT

A fabric comprises first and second webs of gel-forming fiber needled to the first and second sides respectively of a textile fiber scrim. Such fabrics find application as wound dressings, in particular for packing cavity wounds.

9 Claims, No Drawings

NONWOVEN FABRICS AND THEIR MANUFACTURE AND USE

CROSS REFERENCE TO RELATED APPLICATIONS

This application is a 35 USC §371 of International Patent Application No. PCT/GB99/01945, filed Jun. 21, 1999, which claims priority of Great Britain Application No. 9813429.6, filed Jun. 23, 1998.

FIELD OF THE INVENTION

This invention relates to nonwoven fabrics which comprise gel-forming fibres, useful in the field of wound dressings, in particular the field of cavity wound dressings, and to methods of manufacturing such fabrics. It is an object of the invention to provide improved dressings suitable for packing cavity wounds.

BACKGROUND ART

Gel-forming fibres such as alginate fibres and carboxymethylated cellulose fibres are known. Wound dressings of various constructions containing such fibres have been marketed. Treatment of cavity wounds, including the use of dressings, is discussed by C P Berry in an article entitled "Cavity wound management" in J. Wound Care, 1993, vol. 2, no. 1, pp. 29-32 and by A Hallett in an article entitled "Cavity-Wound Management" in Nursing Times, 1995, vol. 91, no. 30, pp. 72, 74 and 79. Dressings for packing cavity wounds are desirably flexible and conformable and capable of removal in one piece after use, without trauma to the patient and without leaving residual fragments of the dressing in the wound. Alginate cavity wound dressings are recommended for moderately and heavily exuding wounds. Such dressings are commonly in the form of a textile sliver and consequently have low mechanical strength and integrity.

Needled nonwoven fabrics (needle-tacked or needle-punched fabrics, needlefelts) of alginate staple fibres have been marketed as wound dressings. Alginate fibres are weak fibres, particularly when wetted, and accordingly a balance must be struck between conflicting desires for mechanical strength and integrity (requiring high-intensity needling and/or high basis weight fabric) and for suppleness (reduced by high-intensity needling and/or the use of high basis weight fabric). If a dressing has poor mechanical strength, a secondary (backing) dressing may be employed; but this is time-consuming and adds extra work and cost when the dressing is applied. Also, use of such secondary dressings is undesirable or inappropriate with dressings for cavity wounds. Alginate dressings having a backing layer affixed with adhesive are known, but they are unsuited for applications such as the treatment of cavity wounds.

WO-A-89/12471 discloses a pad of alginate fibres which have first and second cations (e.g. calcium sodium alginate) and the wetting of such pads prior to their use as wound dressings. The pad may be a needle-punched nonwoven fabric of staple fibre.

EP-A-0,344,913 discloses a hydroentangled fabric of alginate staple fibres and the use thereof as a wound dressing. At low basis weights (less than about 20 or 50 g/m²), the fabric preferably includes a small percentage of reinforcing fibre such as rayon to permit it to be handled easily while saturated with saline water.

EP-A-0,476,576 discloses a nonwoven fabric of alginate staple fibres made by a modified needle-tacking process, in which the leading barb of the needles penetrates into a mat of fibres to a depth of from about 60 to about 99% of the thickness of the mat. These fabrics are said to find use as wound dressings.

U.S. Pat. No. 5,674,524 discloses an alginate dressing having an integral non-alginate backing layer. A web of alginate staple fibre and a backing layer are brought together and needle-punched to yield a composite dressing. Examples are given of a fibrous backing layer which is an acrylic/cotton continuous backing or is an elastic polyurethane foam.

DISCLOSURE OF THE INVENTION

According to a first aspect of the invention, there is provided a fabric which comprises first and second webs of gel-forming fibre needled to the first and second sides respectively of a textile fibre scrim. The first and second webs may be of the same or different fibres and of the same or different basis weights; but they are preferably of the same fibre and basis weight.

Examples of gel-forming fibre for use in the fabric of the invention include carboxymethylcellulose fibres and in particular alginate fibres such as calcium alginate fibres and calcium sodium alginate fibres. The basis weight of each web of gel-forming fibre is preferably in the range from 50 to 250 g/m², often around 100 g/m². The titre of the fibres is preferably in the range from 1 to 5 dtex. Each web may consist of a single type of gel-forming fabric or comprise more than one type of gel-forming fibre.

The gel-forming fibre may be a carboxymethylcellulose fibre having a degree of substitution of at least 0.1 carboxymethyl group per glucose unit, the fibre being derived from solvent-spun cellulose fibre and having an absorbency of at least 8 grams 0.9% (by weight) saline solution measured by the free-swell method and having a tenacity of at least 10 cN/tex. Such fibres are disclosed in WO 93/12275, to which reference may be made for further details.

The textile fibre scrim may be a woven or knitted fabric, but it is preferably a nonwoven fabric, more preferably a thermally-bonded nonwoven fabric of thermoplastic fibres. Examples of suitable thermoplastic fibres include polyamide, polyester and polypropylene. A woven or knitted or non-bonded nonwoven fabric preferably consists of continuous filament yarn to minimise the possibility of textile fibres becoming detached and remaining behind on removal from a wound. Other types of nonwoven fabric may also advantageously consist of continuous filament yarn; in particular, a thermally spunbonded fabric may be used. The basis weight of the scrim is preferably in the range from 20 to 80, more preferably from 30 to 50, g/m². The scrim should be suitable for medical applications, be susceptible to conventional sterilisation procedures such as exposure to ethylene oxide or to electron-beam or gamma-ray irradiation and be suitable for subjection to a needling process.

The fabrics of the invention are useful as wound dressings. The fabrics of the invention have the advantage that their major surfaces consist of gel-forming fibre, so that when they are used as a dressing essentially only the gel-forming fibre comes into contact with the wound.

The fabrics of the invention or one or more components thereof may be medicated.

According to a second aspect of the invention, there is provided a method of manufacturing a nonwoven fabric according to the first aspect of the invention, which method comprises needling together in the specified order a first web of gel-forming fibres, a textile fibre scrim, and a second web of gel-forming fibres. The webs of gel-forming fibres may be prepared by conventional carding and cross-lapping equipment and techniques, and the fabric may be formed using conventional needle-punching equipment and techniques.

When a web consisting of gel-forming fibre is needled, it is often found that the basis weight of the needled fabric is less than that of the web; i.e. the web stretches during needling and there is a concurrent reduction in width. This may cause difficulties in process control. The method of the invention has the advantage that little or no such stretching occurs.

According to a third aspect of the invention, there is provided a wound dressing which comprises a fabric according to the first aspect of the invention. For treatment of cavity wounds, the dressing is preferably in the form of a ribbon of width in the range from 0.5 to 5 cm, further preferably provided for use in roll form. The ability to produce narrow ribbons, preferably of width in the range from 0.5 to 2 cm, or from 0.5 to 1 cm, of good mechanical strength is advantageous, because such a ribbon is useful in packing narrow cavity wounds (e.g. a sinus or fistula). The linear weight of such a ribbon may be in the range from 30 to 100 g/m (about 1-3 g/30 cm), which is comparable to that of alginate sliver known as a dressing for packing cavity wounds. We have found that ribbons of conventional needlefelt made of gel-forming fibre having width less than about 2.5 cm tend to be weak when wetted, whereby there is an undesirable risk that they will break during removal from a wound.

The invention is illustrated by the following Examples, in which parts and proportions are by weight unless otherwise specified:—

Example 1

A comparative fabric sample was made in conventional manner by needling together three cross-laid carded webs of calcium alginate staple fibre (fibre 2.5 dtex, 50 mm staple length, available from Akzo Nobel UK Ltd, formerly Courtaulds plc; web basis weight 135 g/m$^2$; fabric basis weight 330 g/m$^2$). Samples of fabric according to the invention were made by laying-up cross-laid carded webs of the same alginate staple fibre (nominal basis weight 100 g/m$^2$) either side of a spunbonded (thermally-bonded continuous filament) polyester or polyamide fabric (scrim) (nominal basis weight 50 g/m$^2$; available from Lantor (UK) Ltd.) and needling the assembled webs and fabric together. The intensity of needling was lower than in the comparative sample. The fabrics were cut into 30×2 cm strips suitable for use in packing cavity wounds. Fabric absorbency was measured by the method described in British Pharmacopoeia 1993, Addendum 1995, page 1706 for Alginate Packing using 5×2 cm samples. Other physical properties were measured in conventional manner. The results are presented in Table 1:

TABLE 1

| Sample | Alginate (comparative) | Alginate/ Polyester | Alginate/ Polyamide |
|---|---|---|---|
| Basis weight g/m$^2$ | 330 (14) | 255 (9) | 271 (10) |
| Thickness mm | 4.7 (0.2) | 3.9 (0.1) | 3.8 (0.2) |
| Tensile strength (dry) N/cm | 8.0 (0.9) | 5.4 (1.0) | 27.9 (1.6) |
| Tensile strength (wet) N/cm | 3.5 (0.3) | 7.6 (0.7) | 22.6 (2.5) |
| Absorbency g/g | 10.0 (0.9) | 13.3 (0.5) | 12.9 (0.6) |
| Absorbency g/100 cm$^2$ | 33.0 (1.3) | 33.0 (1.0) | 34.2 (1.1) |

All measurements were averages of ten tests. The two series of absorbency measurements were made on different samples. The values in parentheses represent standard deviations.

The absorbency of a carded sliver of the alginate fibre (linear weight 6.6 g/m) was 15 g/g.

The fabrics of the invention were markedly less stiff, softer and more supple than the comparative sample. The fabrics of the invention were markedly stronger than the comparative sample, particularly when wet. The strength of the alginate/polyamide fabric surpassed likely requirements. The fabrics of the invention were of appreciably higher absorbency on weight basis than the comparative fabric, despite the fact that the fabrics of the invention contained about 20% of hydrophobic fibre. The fabrics of the invention and the comparative fabric were of similar absorbency on area basis, despite the facts that the weight per unit area of the fabrics of the invention was about 20% lower than that of the comparative fabric and that the weight of alginate per unit area in the fabrics of the invention was about 40% lower than in the comparative fabric.

Example 2

A fabric according to the invention was made by laying-up cross-laid carded and needled webs of carboxymethylcellulose fibre (2.2 dtex, 25 mm, D.S. 0.4; web nominal basis weight 100 g/m$^2$; according to WO93/12275; HYDROCEL, Trade Mark of Akzo Nobel UK Ltd, formerly Courtaulds plc) either side of a spunbonded fabric (nominal basis weight 40 g/m$^2$; polypropylene; available from Freudenberg Nonwovens) and needling the assembled webs and fabric together. The results shown in Table 2 were obtained:

TABLE 2

| Basis weight g/m$^2$ | 233 (8) |
|---|---|
| Thickness mm | 3.4 (0.2) |
| Tensile strength (dry) N/cm | 27.7 (2.6) |
| Tensile strength (wet) N/cm | 15.4 (1.8) |
| Absorbency g/g | 12.4 (0.3) |
| Absorbency g/100 cm$^2$ | 28.9 (0.5) |

All measurements were averages of ten tests. The values in parentheses represent standard deviations.

The invention claimed is:

1. A narrow ribbon dressing for packing a cavity wound comprising fabric which includes a first web of gel-forming fiber needled to one side of a textile fiber scrim formed from a thermally-bonded nonwoven fabric consisting of thermoplastic fibres of continuous filament material, and a second web of said gel-forming fiber needled to an opposite side of said textile fiber scrim, wherein said scrim fabric has a weight in the range of between 20 g/m$^2$ and 80 g/m$^2$, said first web of gel-forming fiber has a weight in the range of between 50 g/m$^2$ and 250 g/m$^2$ and wherein said first and second gel-forming fiber webs each comprise fibers entangled with said textile fiber scrim such that the resulting fabric forms a narrow ribbon, said ribbon having a width of as little as 0.5 cm, wherein said ribbon has a linear weight/width of at least 580 g/m$^2$ where the linear weight is given in g/m and the width is in meters.

2. A wound dressing ribbon for treatment of cavity wounds, said ribbon being formed of a fabric comprising:

a first web of gel-forming fiber having a basis weight;

a textile fiber scrim formed from a thermally-bonded nonwoven fabric consisting of thermoplastic continuous filament material having a basis weight; and a second web of gel-forming fiber having a basis weight; said first web and said second web being needled to opposite sides of said textile fiber scrim, major surfaces of said opposite sides of said ribbon consisting of said first and second webs of said gel forming fiber, and said ribbon having a linear weight/width of at least 580 g/m², where the linear weight is given in g/m and width is given in meters, first and second gel-forming fiber webs each comprise fibers entangled with said textile fiber scrim such that said ribbon has a width of as little as 0.5 cm.

3. A wound dressing according to claim 2, wherein at least one of said first and second webs of gel-forming fiber and said textile fibre scrim is medicated.

4. A wound dressing according to claim 3, wherein said gel-forming fiber is alginate fiber.

5. A wound dressing according to claim 3, wherein said gel-forming fiber is carboxymethylcellulose fiber.

6. A wound dressing according to claim 5, wherein said carboxymethylcellulose fiber has a degree of substitution of at least 0.1 carboxymethyl group per glucose unit, is derived from solvent-spun cellulose fiber, has an absorbency of at least 8 grams 0.9% saline solution measured by the free-swell method, and has a tenacity of at least 10 cN/tex.

7. A method of manufacturing a wound dressing fabric ribbon, comprising the steps of: needling together, in the specified order, a first web of gel-forming fibers to one side of a textile fiber scrim formed from a thermally-bonded non-woven fabric consisting of thermoplastic continuous filament material, and needling a second web of gel-forming fibers to an opposite side of said textile fiber scrim to form a needled web having its major surfaces consisting of said gel forming fibers; and forming said needled web into a ribbon having a linear weight/width of at least 580 g/m²; wherein the linear weight is given in g/m; and wherein first and second webs each comprise fibers entangled with said textile fiber scrim such that said ribbon may have a width of as little as 0.5 cm.

8. The dressing of claim 2 wherein the width of said ribbon is in the range from about 0.5 cm to 2 cm.

9. The dressing of claim 2 wherein the width of said ribbon is in the range from about 0.5 cm to 1 cm.

* * * * *